United States Patent [19]

Komatsu et al.

[11] Patent Number: 5,631,317
[45] Date of Patent: *May 20, 1997

[54] PROCESS FOR PRODUCING SELF-DISPERSING AND SALT-SENSITIVE POLYMER

[75] Inventors: Masanori Komatsu; Ikuko Toki, both of Tokyo, Japan

[73] Assignee: Lion Corporation, Tokyo, Japan

[*] Notice: The term of this patent shall not extend beyond the expiration date of Pat. No. 5,312,883.

[21] Appl. No.: 161,795

[22] Filed: Dec. 6, 1993

[30] Foreign Application Priority Data

Dec. 10, 1992 [JP] Japan ..................... 4-330751

[51] Int. Cl.$^6$ ..................... C08L 33/06
[52] U.S. Cl. ..................... 524/561; 524/833
[58] Field of Search ..................... 524/561, 833; 526/318.44

[56] References Cited

U.S. PATENT DOCUMENTS

| | | | |
|---|---|---|---|
| 3,804,092 | 4/1974 | Tune | 128/284 |
| 5,312,883 | 5/1994 | Komatsu et al. | 523/344 |

FOREIGN PATENT DOCUMENTS

| | | |
|---|---|---|
| 58-136647 | 8/1983 | Japan . |
| 63-139906 | 6/1988 | Japan . |
| 63-280702 | 11/1988 | Japan . |
| 3-174417 | 7/1991 | Japan . |

*Primary Examiner*—Jeffrey T. Smith
*Attorney, Agent, or Firm*—Burns, Doane, Swecker & Mathis, LLP

[57] ABSTRACT

Disclosed is a process for producing a self-dispersing and salt-sensitive polymer by polymerizing the following monomers (A), (B) and (C) in a total concentration of 25 % by weight or above:

(A) 35 to 65 % by weight of acrylic acid, (B) 10 to 45 % by weight of a vinyl monomer represented by the following general formula [I]:

$$CH_2=C(R^1)COOR^2 \qquad [I]$$

wherein $R^1$ represents a hydrogen atom or a methyl group; and $R^2$ represents an alkyl group having 8 to 12 carbon atoms, and (C) 20 to 45% by weight of a vinyl monomer represented by the following general formula [II]:

$$CH_2=C(R^3)COOR^4 \qquad [II]$$

wherein $R^3$ represents a hydrogen atom or a methyl group; and $R^4$ represents an alkyl group having 2 to 4 carbon atoms in a mixed solvent comprising 50 to 90% by weight of an organic solvent having a solubility parameter of 10 $(cal/cm^3)^{1/2}$ or below and miscible with water and 50 to 10% by weight of water, neutralizing 2 to 15 molar % of the acrylic acid moiety of the polymer, distilling off the organic solvent while water is left, and further adding water thereto. The polymer produced by the process is soluble in tap water, but insoluble in an aqueous salt solution of a low concentration such as 0.2% aqueous salt solution. In case the polymer is used as a binder for a non-woven fabric or paper, it exhibits satisfactory strength and permeability to a body fluid when the resultant product is wet with the body fluid.

14 Claims, No Drawings

PROCESS FOR PRODUCING SELF-DISPERSING AND SALT-SENSITIVE POLYMER

BACKGROUND OF THE INVENTION

The present invention relates to a process for producing a self-dispersing and salt-sensitive polymer having such characteristic properties that it is soluble or dispersible in a usual tap water but is insoluble in water containing not less than 0.2% by weight of neutral inorganic salts (such as sodium chloride, potassium chloride, sodium sulfate and potassium sulfate).

It is known that most polymer emulsions are produced by an emulsion polymerization process and that an emulsifier used in the process will impair the capacity and properties of the film after drying. Japanese Patent Unexamined Published Application (hereinafter referred to as "J. P. KOKAI") Nos. Sho 58-136647 and Sho 63-280702 disclose processes for solving this problem, which comprise conducting the polymerization in an organic solvent, distilling off the organic solvent and adding water to the residue to conduct the self-dispersion. However, these processes are for the production of essentially water-insoluble polymers, and as described in Examples given in the specifications, films prepared from such a polymer emulsion are not dissolved or dispersed even when they are immersed in water.

On the other hand, it has been known that when an inorganic salt which is an electrolyte is added to an aqueous solution of a water-soluble polymer, the polymer is salted out to form a precipitate. On the other hand, it has been known that salts are contained in human body fluids such as urine in an amount of at least about 0.5% by weight (hereinafter referred to as "%", otherwise specified). It is supposed, therefore, that when a non-woven fabric or paper is bonded by means of a binder comprising a polymer which is soluble or dispersible in tap water but insoluble in an aqueous solution containing salts in an amount of about 0.5% by weight, the resulting product will have a sufficient strength when it is brought into contact with a body fluid, but the product will be easily dispersed in a flush toilet. Under these circumstances, investigations are made on the use of the salt-sensitive polymer as a binder for various products to be thrown into the flush toilet or the like. Among the salt-sensitive polymers, anionic polymers such as sodium salts of polyacrylic acid and carboxymethyl cellulose are less sensitive to an increase in the concentration of an electrolyte in an aqueous solution. Such anionic polymers become insoluble in, for instance, an aqueous solution of common salt when the common salt concentration is increased to as high as 4 to 5% or above. Although J. P. KOKAI No. Sho 50-52371 discloses an alkali cellulose ether sulfate, the difference between the solubility of this sulfate in tap water and that in 0.5% aqueous common salt solution is not clearly described in this patent. Moreover, since the alkali cellulose ether sulfate is prepared by sulfating a cellulose derivative such as ethyl cellulose, the polymer used as the starting material is relatively expensive.

As for a salt-sensitive polymer for solving the foregoing problems, J. P. KOKAI No. Sho 63-139906 discloses a partially neutralized copolymer of (meth)acrylic acid and a (meth)acrylic ester as the polymer soluble in tap water but insoluble in an aqueous solution of common salt having a concentration of not less than 0.5%. However, such a partially neutralized copolymer has a high adhesion. J. P. KOKAI No. Hei 3-174417 discloses a partially neutralized copolymer of (meth) acrylic acid and an aryl or cycloalkyl (meth)acrylate; or a partially neutralized copolymer of (meth)acrylic acid and a styrene derivative which copolymers have no problem of the adhesion. However, non-woven fabrics or papers prepared by using such a polymer as the binder do not have satisfactory strength and permeability to the body fluid practically demanded when they are wetted with the body fluid. Namely, when the strength of the non-woven fabrics or papers is sufficiently increased, the water-repellency of the polymer becomes excessively high and the permeability to the fluid is reduced. On the contrary, when the permeability to the fluid is satisfactorily increased, the strength of a film or the like prepared from the polymer becomes insufficient. Salt-sensitive binders disclosed in J. P. KOKAI Nos. sho 63-139906 and Hei 3-174417 are used in the form of a solution in a mixed solvent of an organic solvent such as acetone or methanol with water. When such a binder is used as the binder for non-woven fabrics or papers, it poses problems such as smell and safety, e.g. fire.

SUMMARY OF THE INVENTION

A primary object of the present invention is to provide a process for producing a salt-sensitive polymer which is insoluble in an aqueous salt solution of a low concentration such as 0.2%.

Another object of the present invention is to provide a process for producing a salt-sensitive polymer which has satisfactory strength and permeability to the body fluid when it is used as a binder for non-woven fabric or paper.

These and other objects of the present invention will be apparent from the following description and Examples.

The present invention has been completed on the basis of a finding that the above-described problem can be solved by copolymerizing acrylic acid and two or more specified (meth)acrylic esters as the monomers in a specified ratio while the total amount of the monomers is kept above a specified concentration in a mixed solution of a specified organic solvent and water, then neutralizing a specified rate of the acrylic acid moiety, distilling off the organic solvent used for the polymerization, and adding water to obtain the resultant polymer in the aqueous medium.

According to the present invention, there is provided a process for producing a self-dispersing and salt-sensitive polymer by polymerizing the following monomers (A), (B) and (C) in a total concentration of 25% by weight or above:

(A) 35 to 65% by weight of acrylic acid, (B) 10 to 45% by weight of a vinyl monomer represented by the following general formula [I]:

$$CH_2=C(R^1)COOR^2 \qquad [I]$$

wherein $R^1$ represents a hydrogen atom or a methyl group; and $R^2$ represents an alkyl group having 8 to 12 carbon atoms, and (C) 20 to 45% by weight of a vinyl monomer represented by the following general formula [II]:

$$CH_2=C(R^3)COOR^4 \qquad [II]$$

wherein $R^3$ represents a hydrogen atom or a methyl group; and $R^4$ represents an alkyl group having 2 to 4 carbon atoms in a mixed solvent comprising 50 to 90% by weight of an organic solvent having a solubility parameter of 10.0 $(cal/cm^3)^{1/2}$ or below and miscible with water and 50 to 10% by weight of water, then neutralizing 2 to 15 molar % of the acrylic acid moiety of the polymer, distilling off the organic solvent while water is left, and further adding water thereto.

The present invention provides also a process for producing a self-dispersing and salt-sensitive polymer by neutralizing 2 to 15 molar % of the acrylic acid moiety of the polymer obtained by the above-described polymerization process, distilling off the organic solvent while water is left in the presence of 1.0% or below, on the basis of the copolymer, of a neutral inorganic salt comprising a monovalent cation, and adding water thereto.

DETAILED DESCRIPTION OF THE PREFERRED EMBODIMENT

The organic solvents usable in the present invention are those miscible with any amount of water and having a solubility parameter of 10.0 $(cal/cm^3)^{1/2}$ or below such as acetone, tetrahydrofuran, 1,4-dioxane, diacetone alcohol, diethylene glycol monomethyl ether and dipropylene glycol. When a solvent having a solubility parameter of above 10.0 $(cal/cm^3)^{1/2}$ such as methanol or ethanol is used, the polymer obtained after distilling such a solvent followed by addition of water is immediately coagulated or, even if the emulsion is once formed, the polymer is coagulated to form a precipitate with time, so that it is impossible to make the formation of the stable, self-dispersing emulsion. It is an indispensable condition of the present invention to use the mixed solvent of the above-specified organic solvent and water. The proportion of them is: 50 to 90%, preferably 60 to 80%, of the organic solvent to 50 to 10%, preferably 40 to 20%, of water. When the mixing ratio of the solvents is outside of this range, the polymer formed by the polymerization reaction is precipitated or coagulated unfavorably as the reaction proceeds.

As for the proportion of the monomers (A), (B) and (C), acrylic acid as the component (A) is used in an amount of 35 to 65%, preferably 45 to 60%, the monomer component (B) is used in an amount of 10 to 45% preferably 15 to 30%, and the monomer component (C) is used in an amount of 20 to 45%, preferably 25 to 35%.

When the amount of acrylic acid as the component (A) exceeds 65%, a precipitate is formed when the organic solvent is distilled off and water is added after the polymerization to make it impossible to obtain the self-dispersing emulsion. In such a case, the polymer is soluble in an aqueous salt solution having a concentration of as low as, for example, 0.2% and, therefore, when it is used as the binder, the resulting non-woven fabric has an insufficient strength when it is wet with a body fluid. On the contrary, when the acrylic acid content of the polymer is below 35%, its solubility or dispersibility in tap water is insufficient. In such a case, when it is used as the binder, the resulting non-woven fabric has a reduced dispersibility in tap water.

When the amount of the monomer as the component (B) exceeds 45%, the solubility or dispersibility of the polymer in tap water is insufficient, and when the polymer is used as the binder, the water-repellency of the polymer is increased to lower the permeability of the non-woven fabric to the liquid. On the contrary, when it is below 10%, the polymer is dissolved in an aqueous salt solution having a concentration of as low as, for example, 0.2% to reduce the strength of the non-woven fabric. In such a case, when the organic solvent is distilled off and water is added to the residue after completion of the polymerization, the coagulation occurs to make the production of the self-dispersing emulsion impossible.

When the amount of the monomer as the component (C) exceeds 45%, the solubility or dispersibility of the resultant polymer in tap water is insufficient to reduce the liquid-permeability of the non-woven fabric. When it is below 20%, on the other hand, the polymer is dissolved in an aqueous salt solution having a concentration of as low as, for example, 0.2% to reduce the strength of the non-woven fabric. In addition, the intended self-dispersing emulsion is not formed unfavorably in such a case.

The (meth)acrylic esters (B) of the general formula [I] preferably used herein include 2-ethylhexyl (meth)acrylate and lauryl (meth)acrylate. They can be used either singly or in combination. The (meth)acrylic esters (C) of the general formula [II] preferably used herein include ethyl (meth) acrylate, isopropyl (meth)acrylate and n-butyl (meth) acrylate. They can be used either singly or in combination.

The stable self-dispersing emulsion cannot be obtained unless the monomer concentration, i.e. the percentage of the sum of the components (A), (B) and (C), based on the sum of the components (A), (B) and (C) and the solvent, is 25% or above during the polymerization. In case the monomer concentration is below 25% during the polymerization, the polymer is coagulated when the organic solvent is distilled off and then water is added or, even when the emulsion is once formed, the polymer is coagulated to form a precipitate with time. The preferred monomer concentration ranges from 30 to 50%.

The degree of neutralization of the moiety of acrylic acid (A) is also important in the present invention. The degree of neutralization is 2 to 15 molar %, preferably 4 to 12 molar %. The neutralizing agent is not particularly limited. The neutralizing agents include, for example, metal hydroxides such as sodium hydroxide and potassium hydroxide and amines such as monoethanolamine and diethanolamine. Particularly preferred are sodium hydroxide and potassium hydroxide. When the degree of neutralization of the moiety of acrylic acid (A) exceeds 15 molar %, the intended emulsion having a high self-dispersibility cannot be obtained, since the coagulation occurs and, in addition, the polymer is dissolved in an aqueous salt solution having a concentration of as low as 0.2% to impair the strength of the non-woven fabric. On the contrary, when the degree of neutralization is below 2 molar %, the solubility or dispersibility of the polymer in tap water is insufficient and, therefore, the non-woven fabric cannot be sufficiently dispersed in the tap water.

When a neutral inorganic salt comprising a monovalent cation such as sodium chloride, in a specified relative amount to the polymer, is contained in the reaction mixture in the step of distilling off the organic solvent used for the polymerization followed by addition of water, the resultant self-dispersing polymer emulsion has a suitably reduced viscosity and it can be easily handled.

Examples of the inorganic salts to be added after the neutralization of the acrylic acid moiety of the polymer include neutral inorganic salts comprising a monovalent cation such as sodium chloride, potassium chloride, sodium bromide, sodium sulfate and potassium sulfate. When a salt comprising a polyvalent cation such as a calcium salt or magnesium salt is added, the polymer is coagulated to make the formation of the self-dispersing emulsion impossible. The amount of the inorganic salt is 0.05 to 1.0%, preferably 0.1 to 0.5%, based on the polymer. When it exceeds 1.0%, the polymer is coagulated to make the formation of the excellent self-dispersing emulsion impossible. The inorganic salt is added in such a manner that it is previously dissolved in water to be added after the distillation-off of the organic solvent used for the polymerization. The concentration of the inorganic salt in water is desirably as low as possible. It is also possible to conduct the polymerization in the presence of a polymerization initiator which forms, as a by-product, such an inorganic salt in the step of neutralizing the polymer. Examples of the initiators used for this purpose include azo initiators such as 2,2'-azobis(2-amidinopropane) dihydrochloride, 2,2'-{2-[N-(2-hydroxyethyl)amidino]propane} dihydrochloride, 2,2'-azobis[2-(5-methyl-2-imidazolin-2-yl)propane] dihydrochloride and 2,2'-azobis[2-(2-imidazolin-2-yl)propane] dihydrochloride. The polymerization initiator is used in such an amount that the amount of the salt formed by the neutralization will not exceed 1.0% based on the polymer. However, when the amount of the initiator is excess, the molecular weight of the resultant polymer lowers to reduce the effect thereof as the binder or to reduce the stability of the self-dispersing emulsion. Therefore, the initiator is used usually in an amount in the range of 0.1 to 0.5 molar % based on the total amount of the monomers. Inorganic salts other than those formed from the initiator are dissolved in ion-exchanged water and the resultant solution can be used at any time in the neutralization step and thereafter.

The polymerization temperature which varies depending on the organic solvent usually ranges from 40° to 90° C., and the polymerization time ranges from about 1 to 7 hours.

After the completion of the reaction, the organic solvent is mainly distilled off, while water is kept in the reaction solvent as far as possible. Therefore, the distillation is preferably conducted at a temperature ranging from the boiling point of the organic solvent to 140° C., such as 70° to 140° C., preferably 70° to 100° C. under a pressure ranging from reduced pressure of 20 mmHg to atmospheric pressure. Water is added when the amount of the organic solvent in the mixed solvent has been reduced to 5% or less, preferably 1% or less. Although the amount of water to be added is not particularly limited, it is preferably such that the water content of the reaction system is 100 to 900 parts by weight, more preferably 150 to 500 parts by weight, for 100 parts by weight of the polymer. In the presence of such an amount of water, the polymer easily self-disperses in water to form an emulsion.

The aqueous dispersion thus obtained can be directly used as the binder for non-woven fabrics or papers, or the dispersion can be dried to form a dry binder, or it can be cast in a mold to form a film having any desired thickness.

According to the process of the present invention, polymers (molecular weight: 100,000 to 1,000,000) soluble or dispersible in ordinary tap water but insoluble in water containing at least 0.2% of an inorganic salt can be easily obtained in the form of an emulsion in which the polymer is self-dispersed. When the polymer is used as the binder, it can be easily handled and it is free from smell due to the organic solvent or danger. The non-woven fabrics and papers thus obtained exhibit sufficient strength and permeation to a body fluid when they are brought into contact with the body fluid. Another characteristic feature of the present invention is that since the binder is dissolved in a flush toilet, the non-woven fabrics and papers are easily dispersed.

Therefore, the self-dispersing polymer emulsion prepared by the present invention is widely usable as a binder or sheet for paper diapers, sanitary goods, surgical bandages and wet tissues to be thrown into a flush toilet.

The following Examples will further illustrate the present invention.

EXAMPLE 1

55 g of acrylic acid, 15 g of 2-ethylhexyl acrylate, 30 g of n-butyl acrylate, 120 g of acetone and 45 g of ion-exchanged water were fed into a 1 l four-necked separable flask provided with a stirrer, reflux condenser and nitrogen-introducing tube to obtain a homogeneous solution. Then nitrogen gas was introduced into the flask through the nitrogen-introducing tube under stirring. 20 minutes after, a solution of a polymerization initiator prepared by dissolving 0.80 g of 2,2'-azobis (2,4-dimethylvaleronitrile) in 20 g of acetone was added to the resultant solution to initiate the polymerization reaction under heating with an oil bath kept at 70° C. After conducting the polymerization at 70° C. for 6 hours in nitrogen gas stream, the reaction mixture was left to cool to 50° C. and then neutralized by dropwise addition of a solution prepared by dissolving 4.46 g of 48% aqueous sodium hydroxide solution in 70 g of ion-exchanged water with a dropping funnel for 15 minutes. The neutralization rate was 7 molar % based on acrylic acid. After the completion of the neutralization, the reflux condenser was detached and then a branched joint and Liebig condenser were mounted onto the flask. The flask was heated with an oil bath at 100° C. to distill off acetone. When the distillation rate of acetone lowered, the temperature of the oil bath was further elevated to 125° C. The distillation was continued until no more acetone smell had been recognized in the flask. The time necessitated for the operation was 3.5 hours in total and the amount of the distillate was 150 g. 350 g of ion-exchanged water was added to the residue remaining after the distillation of acetone, and the resultant mixture was stirred under heating to 90° C. with an oil bath. The obtained homogeneous mixture was further stirred and cooled to room temperature to obtain a bluish white, opalescent polymer emulsion. The emulsion had a solid content of 17.9% (determined by Kett moisture determination method), viscosity of 500 cps (determined with a BL viscometer at 25° C.) and acetone content of 0.2%. The weight-average molecular weight of the polymer was 330,000.

10 g of the emulsion was taken and diluted with 10 g of ion-exchanged water. 5 g of the diluted emulsion was cast in a 10 cm×10 cm square enclosure formed with a silicone rubber on a polyethylene plate placed on a horizontal table. The emulsion was kept in an air-conditioned conditioned room at 25° C. and at a relative humidity of 50% for three days to obtain a film having a thickness of 30 to 45 μm. The solubility test of the thus-obtained film was conducted by a method which will be described below. In the test, the polymer film was soluble in tap water but insoluble in 0.2% aqueous common salt solution.

Solubility test

About 0.1 g of the obtained polymer film was taken and placed in a Petri dish containing 100 ml of tap water or 0.2% aqueous common salt solution. The film was left to stand at room temperature under these conditions and a change of the film was observed. After three hours, the results were evaluated as follows: "soluble" indicates that the film was dissolved to form a transparent homogeneous solution, "dispersible" indicates that the film disappeared to form a non-transparent, bluish white, turbid solution, and "insoluble" indicates that no change was found at all or the film was whitened while its shape was maintained.

As the tap water, ion-exchanged water containing 60 mg/l of calcium chloride and 120 mg/l of sodium chloride dissolved therein was used.

EXAMPLE 2

A polymer was produced in the same manner as that of Example 1 except that an initiator solution prepared by dissolving 0.57 g of 2,2'-azobis(2,4-dimethylvaleronitrile) in 20 g of acetone was used, and then the polyer was neutralized (nutralization rate: 7 molar % based on acrylic acid).

After completion of the neutralization, acetone was distilled off in the same manner as that of Example 1. The time necessitated was 3 hours and 15 minutes, and the amount of the distillate was 148 g.

After completion of the distillation, a solution of 0.20 g of common salt in 350 g of ion-exchanged water was added to the reaction mixture and the resultant mixture was stirred under heating with an oil bath at 90° C. to obtain a homogeneous mixture. Then the mixture was cooled to room temperature under stirring to obtain a bluish white opalescent polymer emulsion.

The emulsion had a solid content of 18.1% and viscosity of 370 cps (at 25° C. ). The weight-average molecular weight of the polymer was 320,000.

A film was prepared from the emulsion and the solubility thereof was tested in the same manner as that of Example 1. It was soluble in tap water and insoluble in 0.2% aqueous common salt solution.

EXAMPLE 3

A polymer was produced in the same manner as that of Example 1 except that 120 g of acetone and 45 g of ion-exchanged water were replaced with 140 g of acetone and 30 g of ion-exchanged water, respectively, and that an initiator solution prepared by dissolving 0.88 g of 2,2'-azobis (2-amidinopropane) dihydrochloride in 15 g of ion-exchanged water was used, and then the polymer was neutralized and the salt was prepared (nutralization rate: 7 molar % based on acrylic acid).

After completion of the neutralization, acetone was distilled off in the same manner as that of Example 1. The necessitated time was 3 hours, and the amount of the distillate was 151 g. In this connection, an amount of NaCl present at the distillation was 0.38 wt. % relative to the total amount of monomers. After completion of the distillation, 350 g of ion-exchanged water was added to the reaction mixture and the resultant mixture was treated in the same manner as that of Example 1 to obtain a bluish white opalescent polymer emulsion.

The emulsion had a solid content of 18.1% and viscosity of 230 cps (at 25° C. ). The weight-average molecular weight of the polymer was 270,000.

A film was prepared from the emulsion and the solubility thereof was tested in the same manner as that of Example 1. It was soluble in tap water and insoluble in 0.2% aqueous common salt solution.

EXAMPLE 4

55 g of acrylic acid, 15 g of 2-ethylhexyl acrylate, 30 g of n-butyl acrylate, 140 g of tetrahydrofuran and 30 g of ion-exchanged water were fed into a four-necked separable flask provided with a stirrer, reflux condenser and nitrogen-introducing tube to obtain a homogeneous solution. Then nitrogen gas was introduced into the flask through the nitrogen-introducing tube under stirring. 20 minutes after, a solution of a polymerization initiator prepared by dissolving 0.88 g of 2,2'-azobis(2-amidinopropane) dihydrochloride in 15 g of ion-exchanged water was added to the resultant solution to initiate the polymerization reaction under heating with an oil bath kept at 80° C. After conducting the polymerization at 80° C. for 5 hours in nitrogen gas stream, the reaction mixture was left to cool to 50° C. and then neutralized by dropwise addition of a solution prepared by dissolving 4.46 g of 28 wt. % aqueous sodium hydroxide solution in 100 g of ion-changed water for 15 minutes. The neutralization rate was 7 molar % based on acrylic acid.

After the completion of the neutralization, the reaction mixture was heated with an oil bath at 110° C. to initiate the distillation-off of tetrahydrofuran. The distillation was continued for 3 hours by elevating the temperature of the oil bath to 125° C. In this connection, an amount of NaCl present at the distillation was 0.38 wt. % relative to the total amount of monomers. The reaction mixture was once cooled to 50° C. and then distilled with an aspirator under reduced pressure for 1.5 hours. The total amount of the distillate was 175 g. Then 350 g of ion-exchanged water was added to the product. After the same treatment as that of Example 1, a bluish white, opalescent polymer emulsion was obtained.

The emulsion had a solid content of 18.8% and a viscosity of 700 cps (determined at 25° C. ). The weight-average molecular weight of the polymer was 210,000.

A film was prepared from the emulsion and the solubility thereof was tested in the same manner as that of Example 1. It was dispersible in tap water and insoluble in 0.2% aqueous common salt solution.

COMPARATIVE EXAMPLE 1

The polymerization and neutralization were conducted in the same manner as that of Example 1 except that acetone was replaced with ethanol. After completion of the neutralization, ethanol was distilled off by heating (the final temperature of the oil bath: 125° C.) for 3 hours and then distillation with an aspirator at a bath temperature of 50° C. under reduced pressure for 1 hour. The total amount of the distillate was 167 g. Then 370 g of ion-exchanged water was added to the reaction mixture, and the resultant mixture was heated with an oil bath having a temperature of 90° C. and stirred to obtain the homogeneous mixture. Although the resultant product was cooled to room temperature under stirring, the mass of the polymer in the form of a paste adhered to the stirring blades and thus no emulsion could be obtained.

COMPARATIVE EXAMPLE 2

44 g of acrylic acid, 12 g of 2-ethylhexyl acrylate, 24 g of n-butyl acrylate, 192 g of acetone and 72 g of ion-exchanged water were fed into a 1 l four-necked separable flask provided with a stirrer, reflux condenser and nitrogen-introducing tube to obtain a homogeneous solution. Then nitrogen gas was introduced into the flask through the nitrogen-introducing tube under stirring. 20 minutes after, a solution of a polymerization initiator prepared by dissolving 0.64 g of 2,2'-azobis(2,-dimethylvaleronitrile) in 2 g of acetone was added to the resultant solution to initiate the polymerization reaction under heating with an oil bath kept at 70° C. After conducting the polymerization at 70° C. for 6 hours in nitrogen gas stream, the reaction mixture was left to cool to 50° C. and then neutralized by dropwise addition of a solution prepared by dissolving 3.56 g of 48% aqueous sodium hydroxide solution in 70 g of ion-exchanged water for 15 minutes. The neutralization rate was 7 molar % based on acrylic acid. After the completion of the neutralization, acetone was distilled off in the same manner as that of Example 1 (the time necessitated was 4 hours and the amount of the distillate was 238 g). Then 250 g of ion-exchanged water was added to the product. After the same treatment as that of Example 1, a white emulsion was obtained. After leaving the emulsion to stand at room temperature for one day, the polymer was coagulated to form a pasty precipitate, which caused the division of the product into layers.

EXAMPLE 5

A bluish white opalescent polymer emulsion was prepared from 50 g of acrylic acid, 20 g of 2-ethylhexyl acrylate and 30 g of n-butyl acrylate in the same manner as that of Example 3 except that 0.99 g of 2,2'-azobis(2-amidinopropane) dihydrochloride was used as the initiator and 4.63 g of 48 wt. % sodium hydroxide solution (neutralization rate: 8 molar % based on acrylic acid) was used as the neutralizing agent. In this connection, an amount of NaCl present at the distillation was 0.43 wt. % relative to the total amount of monomers.

The emulsion had a solid content of 18.2% and a viscosity of 65 cps (determined at 25° C.). The weight-average molecular weight of the polymer was 200,000.

A film was prepared from the emulsion and the solubility thereof was tested in the same manner as that of Example 1. It was soluble in tap water and insoluble in 0.2% aqueous common salt solution.

EXAMPLE 6

A polymer emulsion was prepared from 55 g of acrylic acid, 10 g of 2-ethylhexyl methacrylate and 35 g of ethyl methacrylate in the same manner as that of Example 1 except that 0.83 g of 2,2'-azobis(2,4-dimethylvaleronitrile) was used as the initiator and 5.73 g of 48 wt. % sodium hydroxide solution (neutralization rate: 9 molar % based on acrylic acid) was used as the neutralizing agent.

The emulsion had a solid content of 17.7% and a viscosity of 280 cps (determined at 25° C. ). The weight-average molecular weight of the polymer was 260,000.

A film was prepared from the emulsion and the solubility thereof was tested in the same manner as that of Example 1. It was soluble in tap water and insoluble in 0.2% aqueous common salt solution.

EXAMPLE 7

A polymer emulsion was prepared from 60 g of acrylic acid, 10 g of lauryl acrylate and 30 g of ethyl acrylate in the same manner as that of Example 1 except that 1.14 g of 2,2'-azobis[2-(2-imidazolin-2-yl) propane] dihydrochloride was used as the initiator and 6.94 g of 48% sodium hydroxide solution (neutralization rate: 10 molar % based on acrylic acid) was used as the neutralizing agent. In this connection, an amount of NaCl present at the distillation was 0.41 wt. % relative to the total amount of monomers.

The emulsion had a solid content of 17.2% and a viscosity of 38 cps (determined at 25° C. ). The weight-average molecular weight of the polymer was 360,000.

A film was prepared from the emulsion and the solubility thereof was tested in the same manner as that of Example 1. It was dispersible in tap water and insoluble in 0.2% aqueous common salt solution.

EXAMPLE 8

A polymer emulsion was prepared from 45 g of acrylic acid, 20 g of 2-ethylhexyl acrylate and 35 g of butyl acrylate in the same manner as that of Example 3 except that 0.82 g of 2,2'-azobis(2-amidinopropane) dihydrochloride was used as the initiator and 6.25 g of 48% sodium hydroxide solution (neutralization rate: 12 molar % based on acrylic acid) was used as the neutralizing agent. In this connection, an amount of NaCl present at the distillation was 0.35 wt. % relative to the total amount of monomers. The emulsion had a solid content of 18.0% and a viscosity of 105 cps (determined at 25° C.). The weight-average molecular weight of the polymer was 180,000.

A film was prepared from the emulsion and the solubility thereof was tested in the same manner as that of Example 1. It was dispersible in tap water and insoluble in 0.2% aqueous common salt solution.

EXAMPLE 9

A polymer emulsion was prepared from 60 g of acrylic acid, 15 g of 2-ethylhexyl acrylate and 25 g of n-butyl acrylate in the same manner as that of Example 3 except that 0.90 g of 2,2'-azobis(2-amidinopropane) dihydrochloride was used as the initiator and 2.78 g of 48% sodium hydroxide solution (neutralization rate: 4 molar % based on acrylic acid) was used as the neutralizing agent. In this connection, an amount of NaCl present at the distillation was 0.39 wt. % relative to the total amount of monomers.

The emulsion had a solid content of 18.2% and a viscosity of 340 cps (determined at 25° C. ). The weight-average molecular weight of the polymer was 380,000.

A film was prepared from the emulsion and the solubility thereof was tested in the same manner as that of Example 1. It was soluble in tap water and insoluble in 0.2% aqueous common salt solution.

COMPARATIVE EXAMPLE 3

It was tried to prepare an emulsion from 70 g of acrylic acid, 10 g of 2-ethylhexyl acrylate and 20 g of n-butyl acrylate in the same manner as that of Example 3 except that 0.97 g of 2,2'-azobis(2-amidinopropane) dihydrochloride was used as the initiator and 5.67 g of 48% sodium hydroxide solution (neutralization rate: 7 molar % based on acrylic acid) was used as the neutralizing agent. In this connection, an amount of NaCl present at the distillation was 0.44 wt. % relative to the total amount of monomers. However, no emulsion could be obtained, since the polymer was homogenerously dissolved to form a solution having an extremely high viscosity. Then 450 g of ion-exchanged water was added to the solution to obtain the aqueous solution having a solid content of 10.1% and a viscosity of 1050 cps (determined at 25° C.). The weight-average molecular weight of the polymer was 450,000.

A film was prepared from this solution and the solubility thereof was tested in the same manner as that of Example 1. It was soluble in both tap water and 0.2% aqueous common salt solution.

COMPARATIVE EXAMPLE 4

A polymer emulsion was prepared from 40 g of acrylic acid, 50 g of 2-ethylhexyl acrylate and 10 g of n-butyl acrylate in the same manner as that of Example 3 except that 0.74 g of 2,2'-azobis(2-amidinopropane) dihydrochloride was used as the initiator and 3.24 g of 48% sodium hydroxide solution (neutralization rate: 7 molar % based on acrylic acid) was used as the neutralizing agent. In this connection, an amount of NaCl present at the distillation was 0.32 wt. % relative to the total amount of monomers. The emulsion thus obtained had a solid content of 17.8% and a viscosity of 180 cps. The weight-average molecular weight of the polymer was 130,000.

A film was prepared from the emulsion and the solubility thereof was tested in the same manner as that of Example 1.

It was insoluble in both tap water and 0.2% aqueous common salt solution.

COMPARATIVE EXAMPLE 5

A polymer emulsion was prepared from 40 g of acrylic acid, 10 g of 2-ethylhexyl acrylate and 50 g of n-butyl acrylate in the same manner as that of Example B except that 0.81 g of 2,2'-azobis(2-amidinopropane) dihydrochloride was used as the initiator and 3.24 g of 48% sodium hydroxide solution (neutralization rate: 7 molar % based on acrylic acid) was used as the neutralizing agent. In this connection, an amount of NaCl present at the distillation was 0.35 wt. % relative to the total amount of monomers. The emulsion thus obtained had a solid content of 18.0% and a viscosity of 280 cps. The weight-average molecular weight of the polymer was 170,000.

A film was prepared from the emulsion and the solubility thereof was tested in the same manner as that of Example 1. It was insoluble in both tap water and 0.2% aqueous common salt solution.

COMPARATIVE EXAMPLE 6

A polymer emulsion was prepared from 30 g of acrylic acid, 25 g of 2-ethylhexyl acrylate and 45 g of n-butyl acrylate in the same manner as that of Example 3 except that 0.74 g of 2,2'-azobis(2-amidinopropane) dihydrochloride was used as the initiator and 2.43 g of 48% sodium hydroxide solution (neutralization rate: 7 molar % based on acrylic acid) was used as the neutralizing agent. In this connection, an amount of NaCl present at the distillation was 0.32 wt. % relative to the total amount of monomers. The emulsion thus obtained had a solid content of 17.7% and a viscosity of 85 cps. The weight-average molecular weight of the polymer was 100,000.

A film was prepared from the emulsion and the solubility thereof was tested in the same manner as that of Example 1. It was insoluble in both tap water and 0.2% aqueous common salt solution.

COMPARATIVE EXAMPLE 7

The same procedure as that of Example 3 was repeated except that 12.73 g of 48% sodium hydroxide solution (neutralization rate: 20 molar % based on acrylic acid) was used. In this connection, an amount of NaCl present at the distillation was 0.38 wt. % relative to the total amount of monomers. The polymer was homogeneously dissolved to form an extremely viscous solution, and thus no emulsion was obtained. 450 g of ion-exchanged water was added to the solution to obtain the homogeneous solution having a solid content of 10.0% and a viscosity of 1200 cps. The weight-average molecular weight of the polymer was 280,000.

A film was prepared from the homogeneous solution and the solubility thereof was tested in the same manner as that of Example 1. It was soluble in both tap water and 0.2% aqueous common salt solution.

COMPARATIVE EXAMPLE 8

The same procedure as that of Example 3 was repeated except that 0.64 g of 48% sodium hydroxide solution (neutralization rate: 1 molar % based on acrylic acid) was used to obtain a polymer emulsion having a solid content of 18.0% and a viscosity of 130 cps. The weight-average molecular weight of the polymer was 250,000. In this connection, an amount of NaCl present at the distillation was 0.38 wt. % relative to the total amount of monomers.

A film was prepared from the emulsion and the solubility thereof was tested in the same manner as that of Example 1. It was insoluble in both tap water and 0.2% aqueous common salt solution.

COMPARATIVE EXAMPLE 9

22.5 g of acrylic acid, 27.5 g of 2-ethylhexyl acrylate, 130 g of acetone and 40 g of ion-exchanged water were fed into a 500 ml four-necked separable flask provided with a stirrer, reflux condenser and nitrogen-introducing tube to obtain a homogeneous solution. Then nitrogen gas was introduced into the flask through the nitrogen-introducing tube under stirring. 20 minutes after, a solution of a polymerization initiator prepared by dissolving 0.57 g of 2,2'-azobis(2,4-dimethylvaleronitrile) in 30 g of acetone was added to the resultant solution to initiate the polymerization reaction under heating with an oil bath kept at 70° C. After conducting the polymerization at 70° C. for 6 hours in nitrogen gas stream, the reaction mixture was left to cool to 50° C. and then neutralized by dropwise addition of a solution prepared by dissolving 1.56 g of 48% aqueous sodium hydroxide solution in 50 g of ion-exchanged water for 15 minutes. The neutralization rate was 6 molar % based on acrylic acid. After the completion of the neutralization, acetone was distilled off in the same manner as that of Example 1 (the time necessitated was 3.5 hours and the amount of the distillate was 168 g).

Then 160 g of ion-exchanged water was added to the product. After the same treatment as that of Example 1, a white emulsion was obtained. After leaving the emulsion to stand at room temperature for one day, the polymer was coagulated to form a pasty precipitate, which caused the division of the product into layers.

250 g of ethanol was added to the emulsion which had been divided in layers to obtain a homogeneous solution having a solid content of 9.0%. The solution was cast in the square enclosure formed with the silicone rubber on the polyethylene plate to form a film and the solubility of the film was tested in the same manner as that described in Example 1. The film was dispersible in tap water but insoluble in 0.2% aqueous common salt solution. The weight-average molecular weight of the polymer was 22,000.

EXAMPLE 10

A web was formed from rayon as the base fiber by carding. The web was then subjected to a water needling treatment and dried to obtain a web having a basis weight of 30 g/m². Then the polymer emulsion or homogeneous solution obtained in each of the above-described Examples and Comparative Examples was diluted with ion-exchanged water to a concentration of 1% by weight. The diluted emulsion or solution was applied, in an amount of 3% by weight based on the base fiber, to the fiber by spray method. The fiber was then dried to obtain the non-woven fabric.

The non-woven fabrics thus obtained were tested as described below. The results are summarized in Table 1.

Wet Strength

The non-woven fabric was cut into pieces of 5 cm×15 cm to obtain the sample. The sample was immersed in an artificial urine having a composition which will be given below for 1 minute and taken out. The water content of the sample was controlled to 150% by absorbing water with a filter paper. The strength of the sample thus treated was determined with a tensile strength tester (MODEL GAC-100 mfd. by Toyo Bouldline Co., Ltd.) at a chuck distance of 10 cm and tensile speed of 100 mm/min.

(Artificial urine)

1.0 wt. % of NaCl, 0.1 wt. % of CaCl$_2$, 0.07 wt. % of MgCl$_2$ and the balance of water.

Permeability to Liquid

The non-woven fabric was cut into pieces of 5 cm×15 cm. The piece was placed on a sheet (10 cm×20 cm) of a filter paper. One drop of the artificial urine was dropped thereon by means of a dropping pipet from a height of about 15 cm, and the time necessitated for the complete passing of the liquid through the non-woven fabric was determined. The criteria were as follows:

○: passed within 2 min,

Δ: passed within 3 min,

×: not passed even after 3 min.

Dispersibility in Water 500 ml of tap water (the same as that described in Example 1) was fed into a 1 l cylindrical vessel with a lid. Pieces of the non-woven fabric having a size of 6 cm×6 cm were thrown into the water. The cylindrical vessel was shaken by means of a shaker at 100 reciprocation/min for 15 min and then the dispersion of the pieces of the non-woven fabric in water was determined on the basis of the following criteria:

○: Dispersion was complete.

Δ: The fabric was broken into pieces to some extent but the dispersion was incomplete.

×: The non-woven fabric remained as it was.

$$CH_2=C(R^1)COOR^2 \quad [I]$$

wherein $R^1$ represents a hydrogen atom or a methyl group; and $R^2$ represents an alkyl group having 8 to 12 carbon atoms, and (C) 20 to 25% by weight of a vinyl monomer represented by the following general formula [II]:

$$CH2=C(R^3)COOR^4 \quad [II]$$

wherein $R^3$ represents a hydrogen atom or a methyl group; and $R^4$ represents an alkyl group having 2 to 4 carbon atoms in a mixed solvent comprising 50 to 90% by weight of an organic solvent having a solubility parameter of 10 (cal/cm$^3$)$^{1/2}$ or below and miscible with water and 50 to 10% by weight of water, then neutralizing 2 to 15 molar % of the acrylic acid moiety of the polymer, distilling off the organic solvent while water is left, and further adding water.

2. The process of claim 1 wherein the total concentration is 30 to 50% by weight.

3. The process of claim 1 wherein amounts of monomers (A), (B) and (C) are 45 to 60% by weight, 15 to 30% by weight and 25 to 35% by weight, respectively.

4. The process of claim 1 wherein the mixed solvent comprises 60 to 80% by weight of the organic solvent and 40 to 20% by weight of water.

5. The process of claim 1 wherein 4 to 12 molar % of the acrylic acid moiety of the polymer is neutralized.

6. The process of claim 1 wherein the component (B) is 2-ethylhexyl (meth)acrylate or lauryl (meth)acrylate.

7. The process of claim 1 wherein the component (C) is at least one compound selected from the group consisting of

TABLE 1

| Sample No. | Composition (wt. %) | Neutralization rate (molar %) | Wet strength (g/5 cm width) | Permeability to liquid | Water dispersibility |
|---|---|---|---|---|---|
| 1 | AAc/2EHA/BA = 55/15/30 | 7 | 450 | ○ | ○ |
| 2 | " | " | 470 | ○ | ○ |
| 3 | " | " | 440 | ○ | ○ |
| 4 | " | " | 410 | ○ | ○ |
| 5 | AAc/2EHA/BA = 50/20/30 | 8 | 530 | ○ | ○ |
| 6 | AAc/2EHMA/BMA = 55/10/35 | 9 | 550 | ○ | ○ |
| 7 | AAc/LA/EA = 60/10/30 | 10 | 630 | ○ | ○ |
| 8 | AAc/2EHA/BA = 45/20/35 | 12 | 610 | ○ | ○ |
| 9 | AAc/2EHA/BA = 60/15/25 | 4 | 420 | ○ | ○ |
| 3* | AAc/2EHA/BA = 70/10/20 | 7 | 300 | ○ | ○ |
| 4* | AAc/2EHA/BA = 40/50/10 | 7 | 670 | × | × |
| 5* | AAc/2EHA/BA = 40/10/50 | 7 | 640 | Δ | × |
| 6* | AAc/2EHA/BA = 30/25/45 | 7 | 600 | × | × |
| 7* | AAc/2EHA/BA = 55/15/30 | 20 | 290 | ○ | ○ |
| 8* | " | 1 | 570 | Δ | × |
| 9* | AAc/2EHA = 45/55 | 6 | 420 | × | Δ |

No. 1 to 9 are Example whereas No. 3* to 9* are comparative Examples.
AAc: acrylic acid, 2EMA: 2-ethylhexyl acrylate, BA: n-butyl acrylate, 2EHMA: 2-ethylhexyl methacrylate, BMA: n-butyl methacrylate, LA: lauryl acrylate, EA: ethyl acrylate.

What is claimed is:

1. A process for producing a self-dispersing and salt-sensitive polymer by polymerizing the following monomers (A), (B) and (C) in a total concentration of 25% by weight or above:

(A) 35 to 65% by weight of acrylic acid, (B) 10 to 45% by weight of a vinyl monomer represented by the following general formula [I]:

ethyl (meth)acrylate, isopropyl (meth)acrylate and n-butyl (meth)acrylate.

8. The process of claim 1 wherein the organic solvent is acetone or tetrahydrofuran.

9. The process of claim 1 wherein the neutralizing agent for neutralizing the acrylic acid moiety is sodium hydroxide.

10. The process of claim 1 wherein the monomers (A), (B) and (C) are polymerized at 40° to 90° C. for about 1 to about 7 hours.

11. The process of claim 1 wherein the organic solvent is distilled off at a temperature ranging from 70° to 120° C. under a pressure ranging from reduced pressure of 20 mmHg to atmospheric pressure.

12. The process of claim 1 wherein water is added after an amount of the organic solvent in the mixed solvent is reduced to 5% or less.

13. The process of claim 1 wherein water is added in such that the water content of reaction system is 100 to 900 parts by weight for 100 parts by weight of the polymer.

14. The process of claim 1 wherein, after the neutralization of the acrylic acid moiety, the organic solvent is distilled off while water is left in the presence of a neutral inorganic salt comprising a monovalent cation in an amount of 0.05 to 1.0% by weight based on the copolymer, and then water is added to the residue.

* * * * *